United States Patent [19]

Fries et al.

[11] 4,341,214
[45] Jul. 27, 1982

[54] SLEEVE-ENCLOSED HYDROPHILIC FOAM TAMPON WITH IMPROVED AFTER-USE WITHDRAWAL CHARACTERISTICS

[75] Inventors: Donald M. Fries, Combined Locks, Wis.; David F. Ring, Morganville, N.J.

[73] Assignee: Kimberly-Clark Corporation, Neenah, Wis.

[21] Appl. No.: 812,174

[22] Filed: Jul. 1, 1977

[51] Int. Cl.³ .......................................... A61F 13/20
[52] U.S. Cl. ................................................. 128/285
[58] Field of Search .................. 128/270, 263, 290 R, 128/290 W, 290 P, 290 B, 290 H, 155, 283, 275, 284, 292 R, 292 W, 292 D, 292 H, 292 B, 285

[56] References Cited

U.S. PATENT DOCUMENTS

| | | | |
|---|---|---|---|
| 1,731,665 | 10/1929 | Huebsch | 128/285 |
| 2,464,640 | 3/1949 | Fourness | 128/290 R |
| 3,749,094 | 7/1973 | Duncan | 128/270 X |
| 3,875,942 | 4/1975 | Roberts et al. | 128/284 X |
| 3,902,493 | 9/1975 | Baier et al. | 128/285 X |
| 3,971,379 | 7/1976 | Chatterjee | 128/290 R X |

FOREIGN PATENT DOCUMENTS 466048  9/1928  Fed. Rep. of Germany ...... 128/270

Primary Examiner—C. Fred Rosenbaum
Attorney, Agent, or Firm—Howard Olevsky; William D. Herrick

[57] ABSTRACT

A catamenial tampon having as the absorbent element a resiliently compressible hydrophilic foam member, including foam-fiber composites, enclosed in an elongate, closed-end sleeve of fluid-permeable sheet material, assembled in a manner to improve withdrawal characteristics after use. The foam member is made up of an oblong rectangular strip of resiliently compressible hydrophilic polyurethane foam curled or rolled up along its length into a shape which proximates that of a hollow right cylinder in which the ends of the curled up foam strip forming the cylinder are in contact or overlap but are free of attachment to each other. The approximate cylindrical shape of the foam member is maintained by confinement inside one end of a loosely-fitting sleeve. The long axis of the sleeve coincides with the axis of the foam cylinder and the sleeve length is substantially greater than the length of the cylinder. The opposite unoccupied end of the sleeve is gathered and secured together to provide a tapered withdrawal end to which a withdrawal string is attached.

12 Claims, 16 Drawing Figures

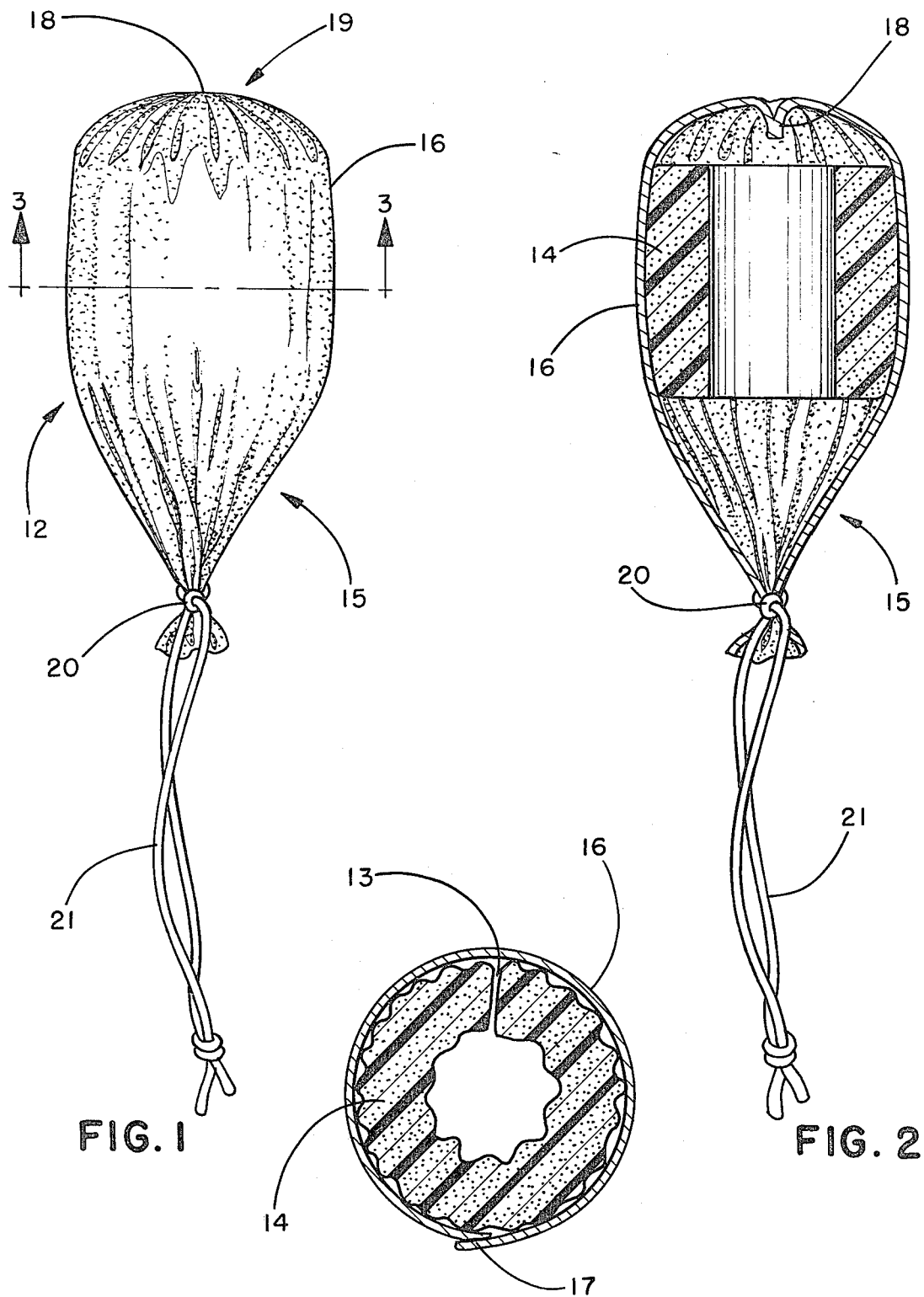

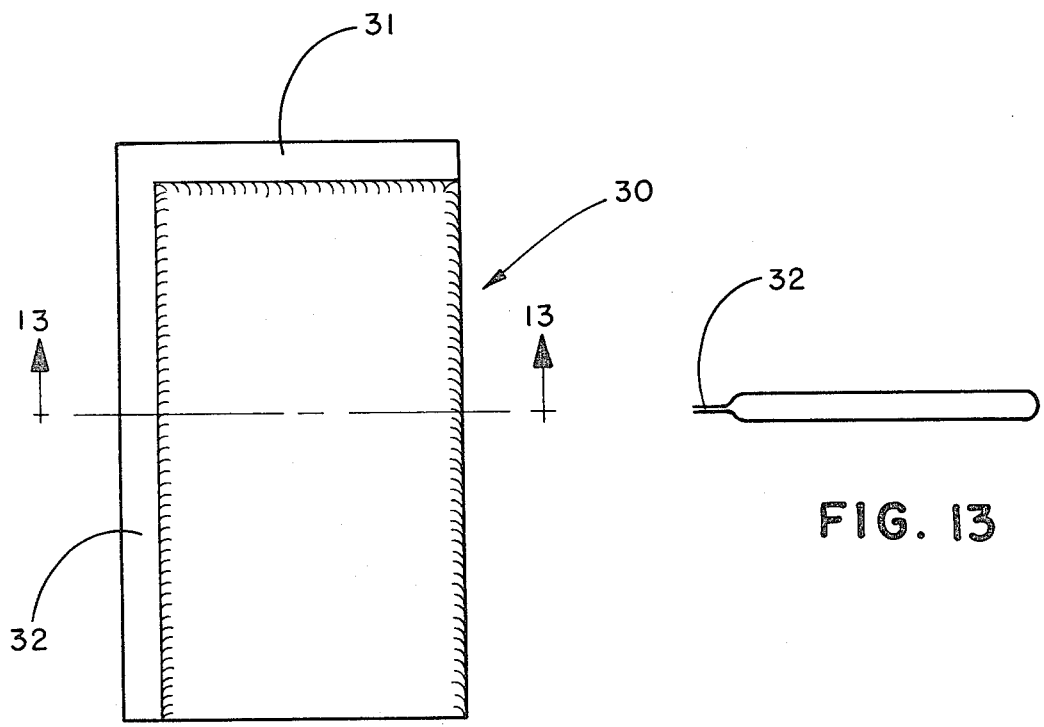
FIG. 12
FIG. 13
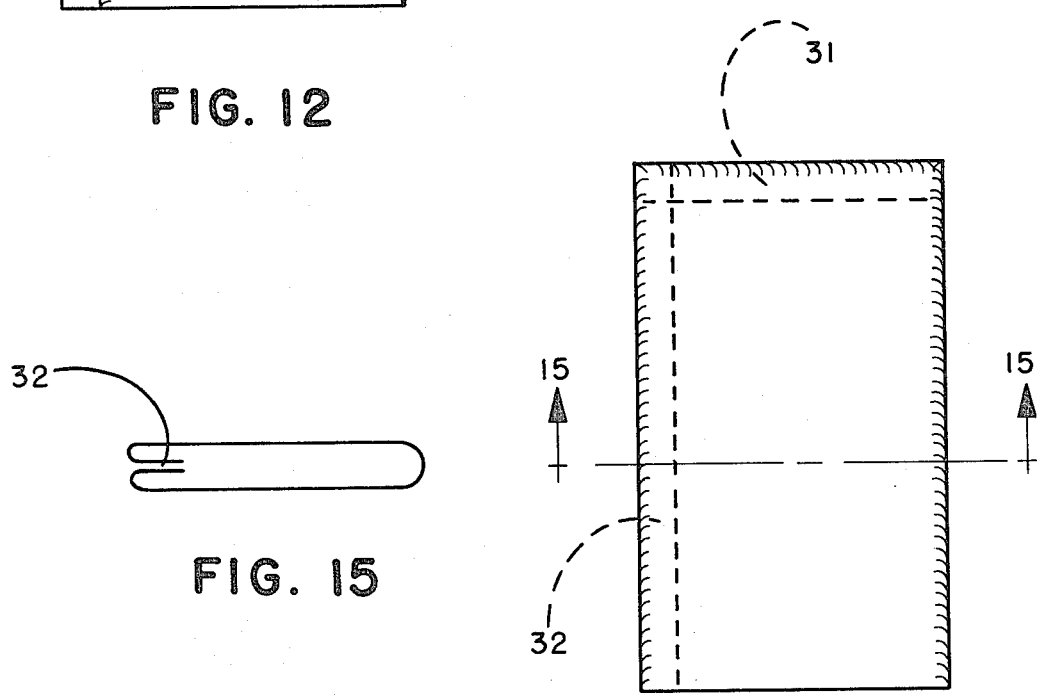
FIG. 15
FIG. 14

SLEEVE-ENCLOSED HYDROPHILIC FOAM TAMPON WITH IMPROVED AFTER-USE WITHDRAWAL CHARACTERISTICS

BACKGROUND OF THE INVENTION

The use of compressively resilient hydrophilic foam members as part of, or as the entire, absorbent body in a catamenial tampon is known in the art. Typical prior art patents in this field include Meynier, Jr. U.S. Pat. No. 2,884,925, Duncan U.S. Pat. No. 3,749,094, Dulle U.S. Pat. No. 3,766,921, Dulle U.S. Pat. No. 3,794,029 and Dulle U.S. Pat. No. 3,856,013. These patents relate generally to tampons in which the absorbent member is made from hydrophilic foam formed into conically shaped absorbent bodies which may have either a hollow, solid, or discontinuous interior structure. Another patent in this field is Schaefer U.S. Pat. No. 3,815,601 which relates to tampons containing an aggregate of separate discrete pieces of low modulus, resilient, absorbent foam encased in a relatively loose overwrap. Still another patent is Dulle U.S. Pat. No. 3,834,389 which utilizes a compressible resilient sponge foam core within a textile mass. While each of these tampon structures is useful in performing its intended function, it has been found that the herein defined combination of a hydrophilic foam core and a fluid permeable sleeve overwrap results in significant improvements with respect to simplified construction, rapidity of intravaginal tampon expansion, conformability during use, absorptive capacity, and particularly, ease of withdrawal after use.

SUMMARY OF THE INVENTION

This invention is directed to a catamenial tampon which utilizes as the main absorbent element an initially flat strip or strips of resiliently compressible, and preferably water-swellable, hydrophilic polyurethane foam rolled into a generally cylindrical shape and enclosed in a fluid-permeable sleeve. Specifically, the absorbent element is comprised of an oblong sheet or slab of hydrophilic foam, which may be in one piece but preferably is multilayered, and which is shaped into a form approximating that of a hollow right cylinder by being rolled up or curled along its long dimension. The axis of the resulting cylinder is perpendicular to the original long dimension of the foam piece and the height of the cylinder is about equal to the short dimension of the foam piece. In its cylindrical form, the ends of the curled up foam sheet are disposed substantially in contact, either abutted or slightly overlapped, but are free of attachment to each other. In its cylindrical form, the foam sheet is circumferentially enclosed within an elongate fluid-permeable sleeve having an internal diameter at least equal to the outer diameter of the otherwise unrestrained foam cylinder. If the foam is of the water-swellable variety, the sleeve preferably has a diameter slightly greater than the uncompressed foam cylinder to allow additional available space into which the foam can expand when aqueous fluids such as body exudates are absorbed during use. The sleeve has a length dimension substantially longer than the length of the foam cylinder, i.e., from 150% to 300% of the cylinder length and is closed off at both ends by suitable means. The foam cylinder is disposed toward one end of the closed sleeve which serves as the leading forward end of the tampon during insertion and wearing, leaving empty a substantial part of the rearward portion of the sleeve which serves as the withdrawal end of the tampon. Attached to the trailing end of the rearward portion of the sleeve is a length of cord or the like, which acts as a withdrawal string, and which may also serve as the means for closing the trailing end of the sleeve. The empty, rearward portion of the sleeve, between the foam cylinder and trailing end where the withdrawal string is attached, becomes conically tapered when pulling force is exerted on the withdrawal string during removal of the used tampon to form a wedge-like end structure. This wedge-like shape first presents to the lower vaginal tract and introitus the narrow end of the wedge at the string connection point, and subsequently presents the widening portion of the wedge as the tampon is withdrawn until the width dimension of the foam cylinder is reached. Thus, the tapered sleeve structure gradually enlarges the introital opening of the vagina as it is drawn therethrough, thereby easing withdrawal.

The fluid-permeable sheet material used as the sleeve, may be of hydrophilic, hydrophobic, or partially hydrophobic material.

BRIEF DESCRIPTION OF THE DRAWINGS

In the drawings:

FIG. 1 is a side view of a tampon made in accordance with this invention.

FIG. 2 is a longitudinal section of FIG. 1.

FIG. 3 is a sectional view taken along line 3—3 of FIG. 1.

FIGS. 12-15 show various views of a simplified construction of sleeves which may be used as part of the tampon.

DETAILED DESCRIPTION OF THE INVENTION

Figure 4:
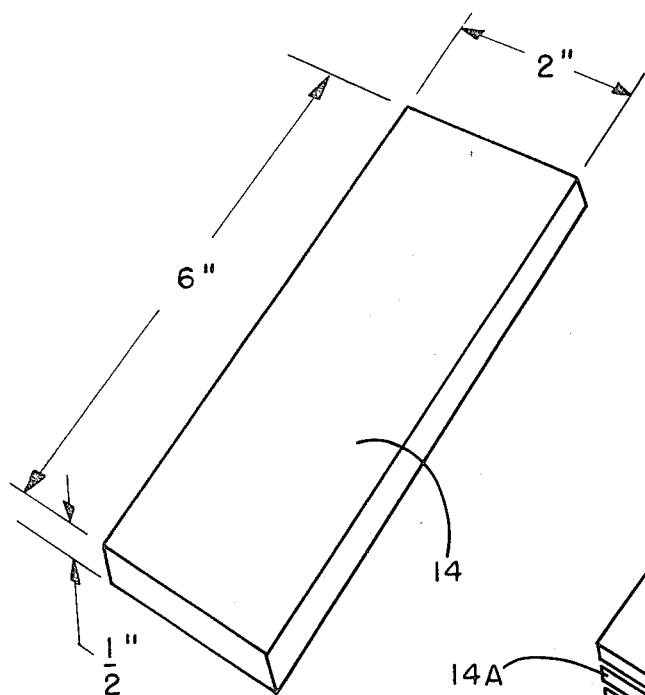
FIG. 4, shown on sheet 3 of the drawings, is a perspective view of an oblong piece of hydrophilic polyurethane foam as used for the absorbent element in the tampon shown in FIGS. 1-3.
Figure 8:
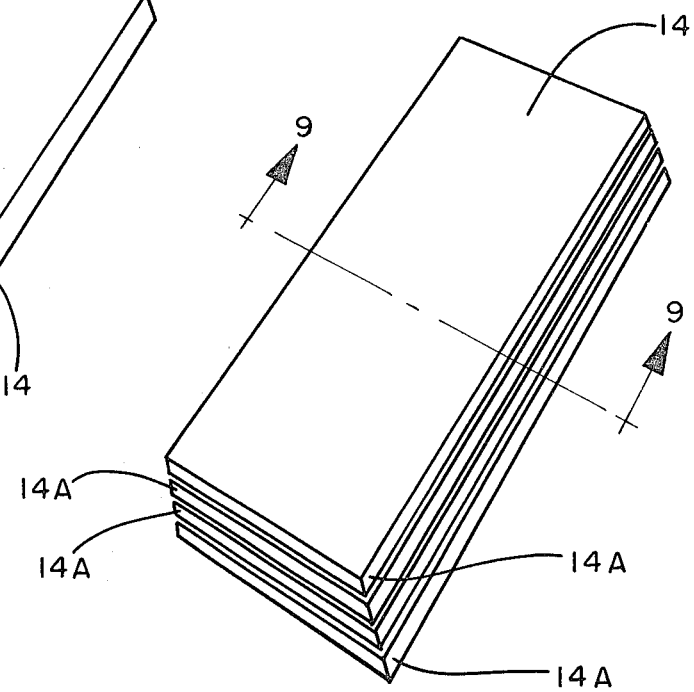
FIG. 8 is a perspective view of a multilayered variation of an oblong polyurethane foam member which may be used as the absorbent in the tampon of this invention.

Referring now to FIGS. 1-4 there is shown a tampon 12 in which the absorbent element is comprised of a flat olong strip of hydrophilic polyurethane foam 14 curled up into a substantially cylindrical shape and enclosed in an elongate fluid-permeable sleeve 16. As shown, the free ends of the curled strip are substantially in abutment, and as indicated at 13, are unattached either to each other or to the outer sleeve. Since the ends of the curled strip of foam are unattached and free to move, with respect to each other the generally cylindrical shape of strip 14 is maintained by being confined within sleeve 16. As may be seen by reference to FIGS. 2 and 3, sleeve 16 is formed from a sheet of web material which is overlapped and sealed adjacent the overlapped edges as at 17 in FIG. 3, and then gathered and closed off at one end 19 by suitable means to form a bag. The bag thus formed is then turned inside out to position the gathered end 18 inside the bag as shown in FIG. 2 to thereby provide a closed leading end 19 free of external protrusions. Sleeve 16 is of a length substantially greater than the length of the cylindrical absorbent element of foam 14 so that the foam 14 does not fill in the entire longitudinal volume of the sleeve when disposed therein. An operable range for the ratio of sleeve length to cylinder length is from about 1.5 to 1, to about 3 to 1. A preferred ratio range is from about 1.8 to 1 to about 2.2 to 1. As indicated in FIG. 2, cylindrical foam element 14 is disposed inside the forward portion of sleeve 16 adjacent the closed leading end 19 at the insertion end of the tampon leaving empty a substantial rearward portion 15 of the sleeve. The trailing end of rearward portion 15 is gathered and closed at 20 where a string 21 or other suitable withdrawal means is attached. String 21 may also serve as the gathering and closure means if desired. Since the sleeve is substantially longer than the cylindrical foam element 14, and since foam element 14 is disposed at the forward end of the sleeve, unoccupied rearward portion 15 of the sleeve between the trailing end of the cylindrical foam element 14 and the gathered trailing end 20 of the sleeve is tapered or conical in section and when in extended condition as shown in FIGS. 1 and 2 provides an effective wedge-like shape, the action of which gradually eases open the introitus as the withdrawal string 21 is pulled during removal of the used tampon. As the tampon is withdrawn, pressure by the introitus against the tapered sleeve section 15 also tends to compress the exit edge of the cylindrical foam element 14 to further ease withdrawal. In this specification, the forward end of the sleeve containing the foam member is also identified as the insertion end portion of the tampon, while the rear of the sleeve the interior of which is unoccupied is also identified as the withdrawal end portion.

Figure 5:
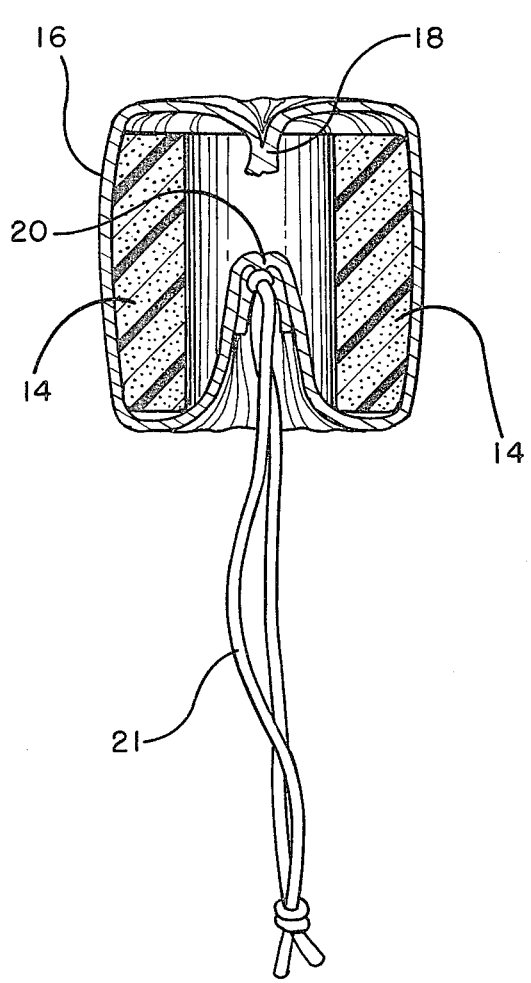
FIG. 5 is a section similar to FIG. 3 but additionally showing the withdrawal end of the tampon sleeve tucked up inside the cylindrical polyurethane core.
Figure 6:
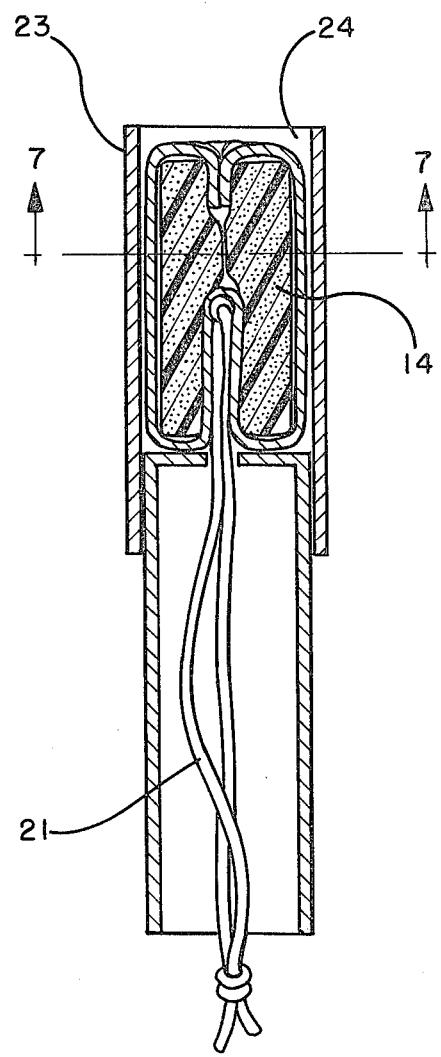
FIG. 6 is a section showing the tampon of FIG. 3 as it appears when compressed and disposed within an insertion device comprised of a pair of telescoping tubes.

In the process of manufacturing the FIGS. 1–7 embodiment, and before the tampon is disposed within an insertion device of the telescoping tubular type, of which many variations are well known in the art and do not need to be described in detail, gathered end 20 of sleeve 16 is preferably tucked up into the interior of the central hollow area of cylindrical element of foam 14 as shown in FIG. 5. Gathered end 18 at the leading end of the tampon of this embodiment may also be tucked inside the forward hollow area of cylindrical foam element 14 and thereby provide the tampon with a smoother insertion tip. After both sleeve ends are tucked in as shown in FIG. 5, the tampon is radially compressed and disposed within the outer tube 23 of a telescoping tube inserter as shown in FIG. 6 and is then ready for use. It is noted that only radial compression occurs when the foam cylinder is squeezed together to fit into the tube since the length of the foam cylinder is established by the width of the starting foam strip. Since only radial compression is employed, there is substantially no length growth of the tampon when compression is released after expulsion from the tube during use. This is advantageous with respect to comfort.

During storage, at the time of insertion, and during normal wear, gathered end 20 will remain tucked up inside the central portion of the cylindrical foam element. However, at the time of withdrawal, when pulling forces are exerted on gathered end 20 by the withdrawal string 21, gathered end 20 quickly everts and the unoccupied trailing portion 15 of the sleeve is thereby formed into the tapered configuration shown in FIGS. 1 and 2, which then interacts with the vaginal orifice in wedge-like fashion to gradually expand the orifice and ease withdrawal.

While the insertion tube 23 is shown as having an open leading end 24 it is understood that the insertion tube may have a tapered closed end comprised of flexible easily opened segments; such inserters also being well known in the art.

Figure 7:
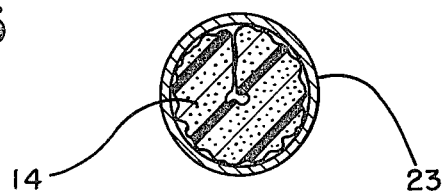
FIG. 7 is a sectional view taken at about line 7—7 of FIG. 6.

When the tampon is radially compressed within the tube 23, the cylindrical element is forced to take on a multiplicity of random or irregular folds and convolutions as indicated in exaggerated form in FIG. 7, in response to the compressive forces to which it is subjected. The elasticity of the foam material nevertheless permits the foam to assume mechanical equilibrium to readily conform to the inner circumference of the tube and provide a relatively smooth tampon surface at the time of ejection.

The mechanics of depositing the tampon of this invention into position within the vagina is conventional. Outer tube 23 is first inserted through the vaginal opening to the desired depth and the tampon is then ejected from the outer tube by telescopic action of the inner tube. Upon ejection from the outer tube and deposition within the vagina, the ejected tampon is relieved of its compressive restraint, permitting the elastic memory of the resilient foam to initiate expansion as it attempts to return to its uncompressed size. The unrestrained foam, even in dry condition gradually tries to expand to its original uncompressed larger cylindrical shape without relying on the action of absorbed fluid which hastens the expansion action. In some cases, as when the foam has been confined in its resiliently compressed state for a long period of time, and especially if it has been sterilized, the foam will tend to take a temporary compression set. However, normal body pressures and movements, as well as the working of the tampon during expulsion from the tube, partially releases such set and permits the dry resilient properties of the foam to take over and allow some gradual expansion before fluid is absorbed. Such early expansion is highly desirable since it serves to allow the foam to begin to fill the vaginal cavity immediately upon deposition therein and thereby minimize potential early bypass leakage by early conformation to internal vaginal contours.

Figure 10:
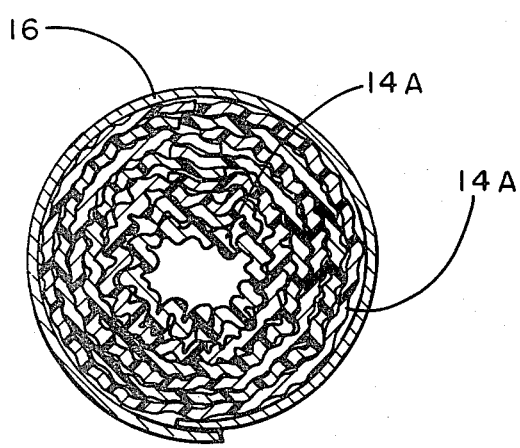
FIG. 10 is a sectional representation similar to FIG. 3 but showing the multilayered polyurethane foam member of FIGS. 8 and 9, as the absorbent element.
Figure 9:
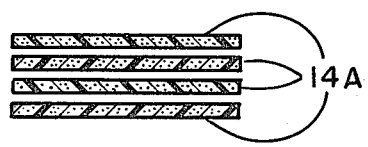
FIG. 9 is a section taken along line 9—9 of FIG. 8.
Figure 11:
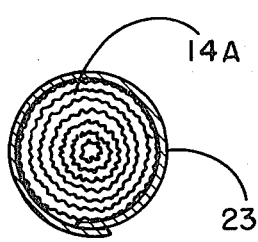
FIG. 11 is a sectional representation similar to FIG. 7 showing the approximate form the multilayered foam member will take when compressed within a tubular insertion device.

In FIGS. 8–11 there is shown a preferred structure for the oblong strip of polyurethane foam utilized in making the cylindrical absorbent element. In this embodiment the oblong strip 14 is comprised of a multiplicity of thin sheets of foam 14a. When this multiple-layered strip is curled up into an uncompressed cylindrical form as shown in FIG. 10, each of the individual thin sheets 14a tend to form a multiplicity of irregular folds and convolutions which are retained when the foam is still further compressed and disposed in a tube as indicated in FIG. 11.

Figure 9A:
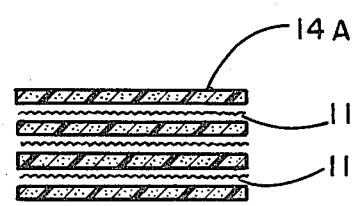
FIG. 9a is similar to FIG. 9 showing another variation of a multilayered embodiment.

This multi-layered structure has an additional advantage in that it permits the inclusion of other materials between plies which can be used to modify, augment and improve performance. For example, while most hydrophilic polyurethane foams have high capacity for fluids, i.e. on the order of 20 to 30 grams of fluid per gram of foam, more effective utilization of the foam's capacity for fluids during use can be obtained by positioning between the foam plies, layers of other material which aid fluid transfer, such as creped tissue, cellulose wadding, rayon fiber, nonwoven webs, high capillarity micro-fibers, or the like. Layers of such fluid transfer material are shown at 11 in FIG. 9a. The presence of these layers enhance the rate of foam expansion due to rapid transfer and distribution of fluid within the tampon cylinder during use. In addition to these fluid transfer layers, other body fluid reactive additives in powdered or fibrous form such as deodorants, fragrances, gelling agents and the like may also be added between foam plies as desired.

As indicated earlier, an absorbent element formed from a single strip or slab of foam as shown in FIGS. 1–4 works well as the resilient absorbent element in the tampon of this invention. However, it has been found that multiple sheets of thinner foam strips generally perform much better than a single layer, and the multilayered structure is therefore the preferred form of the invention. In this regard, it can be generally stated that two plies are better than one, three are better than two, four are better than three, etc. Observed results indicate that the structure having multiple sheets of thinner foam appears to provide a much larger effective surface area for fluid contact because of the existence of a multiplicity of fluid transfer channels between plies. Tampons in which the absorbent member is made from multiple sheets also appear to have greater flexibility and conformability than tampons utilizing thicker one layer sheets. The unattached multi-sheet structure also permits one sheet to move with respect to the other as the individual sheets are distorted and displaced by body pressures, and as the sheets individually expand when fluid is absorbed at various layers and levels. The less restricted multi-sheet structure permits the interior parts of the absorbent member to readjust with respect to each other in response to movements within the vaginal cavity. Multilayered tampons thus expand more readily to permit contact with the rugae and folds of the vaginal walls and thereby minimize the incidence of leakage pathways where fluid bypass might otherwise occur. In other words, the tampon with the multilayered absorbent member more readily maintains optimum contact with vaginal walls thus permitting the foam sheets comprising the absorbent member to operate at their maximum potential ability to prevent leakage as the structure readjusts to fit changing vaginal configurations.

In assembling the tampon of this invention, it is preferred that the extremities of the foam piece or pieces which make up the absorbent element be free to move, i.e. these ends should not be attached to each other or to the sleeve. In forming the cylindrical element, these ends may be in direct abutment, may be slightly spaced from each other, or may be slightly overlapped. However arranged, it is best that the ends be free to move so that the natural elasticity of the material is physically unimpaired allowing relief of tensile or compressive stresses through independent expansion of the strips with minimal thermodynamic work.

As described earlier, with respect to FIGS. 2 and 3, the sleeve overwrap for the tampon may be fabricated by simply gathering one end after overlapped edges are sealed together to form a bag and then turning the bag inside out. Another equally simple structure for the outer wrapper or sleeve is shown in FIGS. 12–15. As shown therein a rectangular sheet 30 is folded in half longitudinally and one end and the free edges are then sealed by heat seal or adhesive as shown at 31 and 32 respectively. The bag thus formed may also be turned inside out as in FIGS. 14 and 15. This provides a neater appearing structure than the end gathering described earlier.

The bag formed from the sleeve material should preferably have an inner diameter which is at least equal to the diameter of the cylindrical absorbent element in its uncompressed dry form to provide sufficient volume for expansion. Preferably, the inner diameter of the bag should be somewhat larger to allow for additional expansion when water-swellable foam is used. If the sleeve diameter or potential volume is adjusted to be equal to the full potential expansion volume of the foam after it has been swelled by body exudates, the full available capacity of the foam will be more readily utilized.

The sleeve material may be made of any fluid-permeable sheet material including woven and non-woven scrim or gauze, non-woven fiber webs of natural or synthetic fibers, spunbonded webs, fibrillated and/or perforated plastic films and the like. An effective material was found to be a spunbonded filamentary web of a hydrophobic polymer such as polyester.

Also as indicated earlier, the material used for the absorbent element is a hydrophilic foam with dry resilience, i.e. an open cell foam which permits fluids to penetrate into the foam and which will spontaneously expand in dry form once compression restraints are removed or a temporary compression set is released. Preferably, the foam should also be water-swellable whereby it will expand beyond its original uncompressed volume when wetted by body exudates. Many types of such foam are now available. When water-swellable foams are contacted with aqueous fluids such as menstrual fluids, the foam tends to swell as the fluid is taken up into the molecular structure in addition to being drawn into the pores by capillary action. When taken up into the foam structure the fluid is maintained in the foam even under squeezing pressure. Foams with various degrees of swelling or tumescence are available, ranging from foams which do not swell at all to others which swell more than 100% or double in size over their original uncompressed volume. Those in the ranges of 50 to 100% are preferred for use in this invention.

One suitable size for the strip or slab of foam for use in the tampon described herein is about six inches long, two inches wide and about ½ inch thick as shown in FIG. 4. Various other sizes may of course be used. When individual plies are used in making up a foam strip of the desired dimension, it is preferred that the individual plies be as thin as possible consistent with economical manufacturing practices. From a performance stand-point, the greater the number of plies used, the better the performance. A good compromise for use in this invention has been found to be a seven ply strip in which the individual plies are about 0.060" thick.

In commercial practice several sizes of tampons are manufactured to accommodate consumer preferences and needs. The most common designations now being used are super and regular sizes, with the super size having the largest capacity for fluids. The weights of the absorbent material employed may vary from about 2.4 grams to about 4.5 grams.

For the tampon described herein weights of from about 1.6 grams of absorbent material for the regular size tampon to about 3.2 grams for the super size tampon have been found to be acceptable in use. Hydrophilic foams having a density in the range of from about 0.12 to 0.25 grams per cubic centimeter are suitable for use in this invention, with 0.18 grams per cubic centimeter being preferred.

What is claimed is:

1. A catamenial tampon comprised of a resiliently compressible absorbent element enclosed in a sleeve of fluid-permeable material, said element being comprised of an oblong strip of hydrophilic foam curled up in the form of a hollow right cylinder with the ends of said strip juxtaposed and with said ends being free of attachment to each other or to said sleeve, said sleeve being elongate and closed at both ends with said closed end sleeve having a length dimension substantially greater than the length of said cylinder and an inner diameter at least equal to the uncompressed outer diameter of said cylinder, the ratio of said closed sleeve length to said cylinder length being in the range of from 1.5 to about 3 to 1; said cylinder being disposed inside one end of said closed sleeve and said end comprising the insertion end portion of said tampon, the other end of said closed sleeve being unoccupied by any absorbent material and comprising the withdrawal end portion of said tampon, said withdrawal end portion being gathered to form a tapered structure, and said withdrawal end portion having a withdrawal string secured to the small gathered end of said tapered structure, enabling said tapered withdrawal end portion to interact in wedge-like fashion with the introital opening of the vagina at the time of withdrawal and to ease such withdrawal when pulling force is exerted on said withdrawal string.

2. The catamenial tampon of claim 1 wherein the free ends of said strip are substantially in abutment.

3. The catamenial tampon of claim 1 wherein the free ends of said strip slightly overlap.

4. The catamenial tampon of claim 1 wherein said oblong strip is comprised of a multiplicity of thin foam layers.

5. The catamenial tampon of claim 4 wherein a fluid transfer material is disposed between said thin foam layers.

6. The catamenial tampon of claim 5 wherein said fluid transfer material is selected from the group consisting of creped tissue, cellulose wadding, rayon fibers and high capillarity micro-fibers.

7. The catamenial tampon of claim 4 wherein a body fluid reactive additive in powdered or fibrous form is disposed between said plies.

8. The catamenial tampon of claim 1 wherein said foam is of the type which swells when aqueous fluids are absorbed.

9. The catamenial tampon of claim 1 wherein said sleeve has a diameter which is slightly greater than the diameter of said cylinder.

10. The catamenial tampon of claim 1 wherein said sleeve is comprised of a non-woven sheet material.

11. The catamenial tampon of claim 10 wherein said sheet material is made from fibers selected from the group consisting of natural and synthetic fibers.

12. The catamenial tampon of claim 11 wherein said sheet material is selected from the group consisting of bonded fiber webs, bonded scrim webs and spunbonded filamentary webs.

* * * * *